United States Patent
Derouet et al.

(10) Patent No.: US 9,839,459 B2
(45) Date of Patent: *Dec. 12, 2017

(54) ASSEMBLY INCLUDING AT LEAST ONE IMPLANT, ONE GRIPPING DEVICE AND ONE ELEMENT FOR THE TRACEABILITY OF THE IMPLANT, AND METHOD FOR TRACEABLY HANDLING THE IMPLANT OF SUCH AN ASSEMBLY

(71) Applicant: NEOSTEO, Nantes (FR)

(72) Inventors: Guillaume Derouet, La Turballe (FR); Maxime Dechelette, Petit Mars (FR)

(73) Assignee: NEOSTEO, Nantes (FR)

( * ) Notice: Subject to any disclaimer, the term of this patent is extended or adjusted under 35 U.S.C. 154(b) by 85 days.

This patent is subject to a terminal disclaimer.

(21) Appl. No.: 14/758,385

(22) PCT Filed: Dec. 20, 2013

(86) PCT No.: PCT/FR2013/053210
§ 371 (c)(1),
(2) Date: Jun. 29, 2015

(87) PCT Pub. No.: WO2014/102491
PCT Pub. Date: Jul. 3, 2014

(65) Prior Publication Data
US 2015/0351845 A1    Dec. 10, 2015

(30) Foreign Application Priority Data

Dec. 31, 2012  (FR) .................................. 12 62987
Dec. 31, 2012  (FR) .................................. 12 62988

(51) Int. Cl.
A61B 19/02    (2006.01)
A61B 17/86    (2006.01)
(Continued)

(52) U.S. Cl.
CPC ............ A61B 17/865 (2013.01); A61B 50/20 (2016.02); A61B 50/30 (2016.02); A61B 90/90 (2016.02); A61B 90/94 (2016.02)

(58) Field of Classification Search
CPC ....... A61B 17/865; A61B 50/20; A61B 50/22; A61B 50/24; A61B 50/30; A61B 90/90; A61B 90/94; A61B 19/026; B65D 85/24
(Continued)

(56) References Cited

U.S. PATENT DOCUMENTS 6,802,421 B1    10/2004  Impellizzeri
8,061,517 B2 *  11/2011  Loeffler ............... A61B 17/865
                                                  206/339

(Continued)

FOREIGN PATENT DOCUMENTS

DE    20 2010 007487 U1    9/2010
EP         1 241 998 A2    11/2004
(Continued)

OTHER PUBLICATIONS

International Search Report, dated Mar. 20, 2014, from corresponding PCT application.

*Primary Examiner* — Andrew Perreault
(74) *Attorney, Agent, or Firm* — Ipsilon USA, LLP

(57) ABSTRACT

A kit of the type including at least an implant (1), a gripper (2) for gripping the implant (1), and a storage element (7) for storing the gripper (7) and its associated implant (1), the storage element (7) including at least one reception location (71) for receiving the gripper (2) and its associated implant (1), and a tracer element (8) for tracing the implant (1). The tracer element (8) is sandwiched between the gripper (2) and the storage element (7), when the gripper (2) and its associated implant (1) are in their stored state in a reception location (71) of the storage element (7).

8 Claims, 6 Drawing Sheets

(51) Int. Cl.
*A61B 19/00* (2006.01)
*A61B 50/20* (2016.01)
*A61B 50/30* (2016.01)
*A61B 90/90* (2016.01)
*A61B 90/94* (2016.01)

(58) Field of Classification Search
USPC ....... 206/339, 438, 223, 570, 571, 338, 363, 206/63.3, 63.5, 564, 368, 370, 369, 804, 206/577
See application file for complete search history.

(56) References Cited

U.S. PATENT DOCUMENTS

2009/0266728 A1 10/2009 Turner et al.
2011/0297571 A1 12/2011 Brand
2013/0000262 A1 1/2013 Richart

FOREIGN PATENT DOCUMENTS

EP      2 392 286 A1   12/2011
FR      2 959 216 A1   10/2011
WO   2009/024189 A2    2/2009

\* cited by examiner

ASSEMBLY INCLUDING AT LEAST ONE IMPLANT, ONE GRIPPING DEVICE AND ONE ELEMENT FOR THE TRACEABILITY OF THE IMPLANT, AND METHOD FOR TRACEABLY HANDLING THE IMPLANT OF SUCH AN ASSEMBLY

The present invention relates to a kit of the type comprising at least an implant, a gripper for gripping said implant, a storage element for storing the gripper and its associated implant, and a tracer element for tracing the implant, and a method of handling, in traceable manner, the implant of such a kit.

Kits of the above-mentioned type are well known to the person skilled in the art, as shown in particular in patent EP 1 241 998.

Generally, and as shown in the prior-art document, identification means for identifying the implant are arranged directly on the gripper. In that embodiment, the surgeon directly takes hold of the gripper associated with its implant and stored in the storage element. The surgeon implants the implant in the human or animal body, and then gives the gripper to the person responsible for traceability. That person reads the information mentioned on the grippers, and generally transfers it onto an electronic or paper medium. As a result, the gripper that potentially might have been contaminated while being implanted must pass from hand to hand at the risk of causing the contamination to be disseminated, whereas it should have been put directly into the bin.

An object of the present invention is thus to propose a kit of the above-mentioned type having a design that makes it possible to avoid transferring the gripper from hand to hand, so as to avoid disseminating any possible contamination.

Another object of the present invention is to propose a kit having a design that makes it possible, if necessary, to handle the implant starting from the storage element and until it is implanted in the human or animal body without touching the implant.

To this end, the invention provides a kit of the type comprising at least an implant, a gripper for gripping said implant, and a storage element for storing the gripper and its associated implant, said storage element including at least one reception location for receiving the gripper and its associated implant, and a tracer element for tracing the implant, the kit being characterized in that the tracer element is sandwiched between the gripper and the storage element, when the gripper and its associated implant are in their stored state in a reception location of the storage element.

Since the tracer element is distinct from the gripper and from the implant and is independent therefrom, it becomes possible to handle the gripper and its associated implant and to transfer the gripper and its associated implant from one location to another without it being necessary simultaneously to transfer the tracer element, which may be the responsibility of another person.

Preferably, the tracer element is in the form of a washer that is provided with identification means for identifying the gripper.

Preferably, the washer presents thickness that lies in the range 0.05 millimeters (mm) to 3 mm.

Preferably, the implant presents a distal end for inserting the implant into the human or animal body, and a proximal end, referred to as the head of the implant, that is suitable for co-operating with a handling tool, the gripper, that is separable from the implant, is in the form of a hollow elongate body that is open at at least one of its ends, and that is slotted longitudinally along at least a portion of its length, the body being made, at least in part, of an elastically-deformable material that tends to return the edges of the slot towards each other, the slot of said body opening out into the axial cavity of said body, inside which the implant is suitable for being inserted, with its distal end projecting from the "distal" end of said body, and the storage element is made up of at least one plate that is provided with at least one cavity that corresponds to a reception location for receiving a gripper that is pre-fitted with its implant.

Preferably, the gripper, which is separable from the implant, is in the form of a hollow elongate body that is open at each of its ends. Preferably, the gripper, which is separable from the implant, is in the form of a hollow elongate body that is slotted longitudinally along its entire length.

In a first embodiment of the invention, the cavity, or at least one of the cavities of the storage element that corresponds to a reception location for receiving a gripper that is pre-fitted with its implant, presents a longitudinal axis that is substantially orthogonal to the surface of said plate, the body of the gripper, inserted axially via its distal end into the cavity, is a stepped tubular body with a shoulder, said outer peripheral shoulder, on going from the distal end towards the proximal end of said body, forming an abutment that limits the extent to which the body can be inserted inside said reception location of the storage element, and the tracer element is sandwiched between the stepped surface of the gripper and the top face of the plate.

In this embodiment, the washer presents an inside diameter that is greater than the outside diameter of the gripper in the zone of the gripper that extends between the distal end and the shoulder of said gripper, and that is less than the outside diameter of the gripper in the zone of the gripper that extends between the proximal end and the shoulder of said gripper.

The zone of the gripper that extends between the distal end and the shoulder of said gripper is interfitted, at least in part, in a cavity of the storage element, with the distal portion of the implant that projects from the gripper extending inside said cavity.

When the implant is in its inserted state in the cavity of the gripper, the head of the implant is at a distance from the proximal end of the gripper.

In a second embodiment of the invention, the cavity, or at least one of the cavities of the storage element that corresponds to a reception location for receiving a gripper that is pre-fitted with its implant, presents a longitudinal axis that is substantially parallel to the surface of said plate, in that the gripper and its implant extend axially inside the cavity, and the tracer element is sandwiched between the proximal end of the gripper and the storage element.

Independently of the embodiment, the axial cavity of the body of the gripper includes a constriction zone for constricting the implant, inside which zone the implant is suitable for being held by being clamped.

Preferably, said kit further comprises means for assisting in separating the gripper from the implant without touching the implant, the means comprising at least one reception sheath for receiving the distal end of the implant, and when its distal end is in its inserted state in the sheath, the implant is separable from its gripper by moving the sheath and the gripper relative to each other in the direction that breaks the alignment between the sheath and the gripper, until the implant passes through the slot of the gripper, said sheath being provided with a bearing seat against which the implant bears both when said implant is in its inserted state in the sheath, and when said implant is in its state separated from its gripper.

In a preferred embodiment, the sheath is mounted securely to the storage element.

Still more preferably, at least one of the cavities of the storage element forms at least a portion of said sheath.

Naturally, the embodiment in which the sheath is independent of the storage element also enters into the field of the present invention.

The invention also provides a method of handling, in traceable manner, an implant of a kit as described above, said implant and its gripper being housed, at least in part, inside a reception location for receiving the storage element, said method being characterized in that it comprises at least a step of manually taking hold of the gripper associated with its implant, until the implant is removed from the reception location, and a step of manually taking hold of the tracer element that is distinct and independent from the gripper and its associated implant, the tracer element being arranged in, or at the inlet of, the reception location of said storage element.

In an implementation of the method in which the kit further comprises means for assisting in separating the gripper from the implant without touching the implant, said method further comprises a step of inserting at least the distal end of the implant while gripped via its gripper into said sheath, a step of separating the implant from its gripper by moving the sheath and the gripper relative to each other in the direction that breaks the alignment between the sheath and the gripper, until the implant passes through the slot of the gripper, and a step of holding the implant in the sheath by bearing against the seat of said sheath until the implant is gripped by a handling tool that can be coupled, preferably by force, with the head of said implant.

The invention can be well understood on reading the following description of embodiment examples, given with reference to the accompanying drawings, in which.

Figure 1:
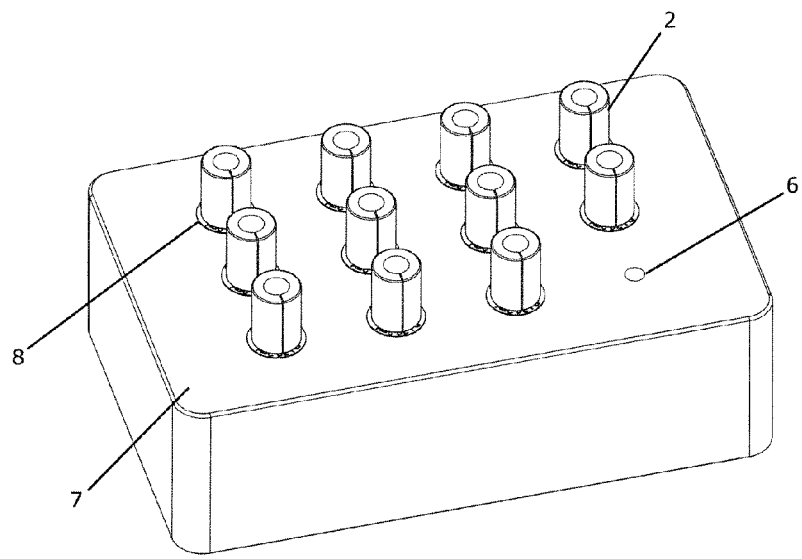
FIGS. 1 to 6 are perspective views showing the various steps of handling an implant and its associated gripper, and the tracer element.

As mentioned above, the kit of the invention is more particularly for making it possible to trace surgical implants 1, such as osteosynthesis implants that are suitable for being implanted in the human or animal body.

The kit thus comprises an implant 1, a gripper 2 for gripping said implant, and a storage element 7 for storing the gripper 2 and its associated implant, said storage element 7 including at least one reception location 71 for receiving the gripper 2 and its associated implant, and a tracer element 8 for tracing the implant. The tracer element 8 for tracing the implant is independent and distinct from the gripper 2 and from its associated implant, so that the gripper and its associated implant may be removed from the reception location of the storage element and transferred into another location without simultaneously transferring the tracer element 8.

In the embodiments shown, the screw-type implant 1 presents a distal end 11 for inserting the implant 1 in the human or animal body, and a proximal end 12, also referred to as the head of the implant, that is suitable for co-operating with a handling tool 9.

The implant head formed by the head of the screw includes a hollow socket into which the end of the handling tool, such as a screwdriver, can be inserted by force, so as to make it possible, when the implant and the handling tool are in their coupled-together state, for the implant to be turned by means of the handling tool, so as to implant it in the human or animal body.

In this embodiment, the gripper 2, which is separable from the implant 1, is in the form of a hollow tubular body 21 that is open at each of its ends, and that is slotted longitudinally along its entire length. The body 21 is made, at least in part, of an elastically-deformable material, such as an elastomer. This material tends to return the edges of the slot 4 towards each other.

The slot 4 of the body 21 opens out into the axial cavity 3 of the body 21, inside which the implant 1 is suitable for being inserted, with its distal end 11 projecting from the distal end of said body 21.

The axial cavity 3 of the body of the gripper 2 includes a constriction zone 31 for constricting the implant, inside which zone the implant 1 is suitable for being held by being clamped.

When the implant is in its inserted state in the cavity of the gripper, the head of the implant is at a distance from the proximal end of the gripper, in particular so as to avoid the surgeon's hand touching the implant while taking hold of the gripper.

In the embodiments shown, the tubular body 21 of the gripper is a stepped body with a shoulder. This shoulder forms an outer peripheral shoulder going from the distal end towards the proximal end of the body 21 of the gripper 2.

The storage element 7 is made up of a plate that is provided with at least one cavity 71 that corresponds to a reception location for receiving a gripper that is pre-fitted with its implant.

The plate may be relatively thick so as to form the body of a box that is closed by a cover. Alternatively, the plate may be inserted into a box body that, likewise, is preferably closed by a cover.

In the embodiments shown in FIGS. 1 to 6, the storage element 7 includes eleven cavities 71 that each serve to receive an implant and its associated gripper.

Figure 9:
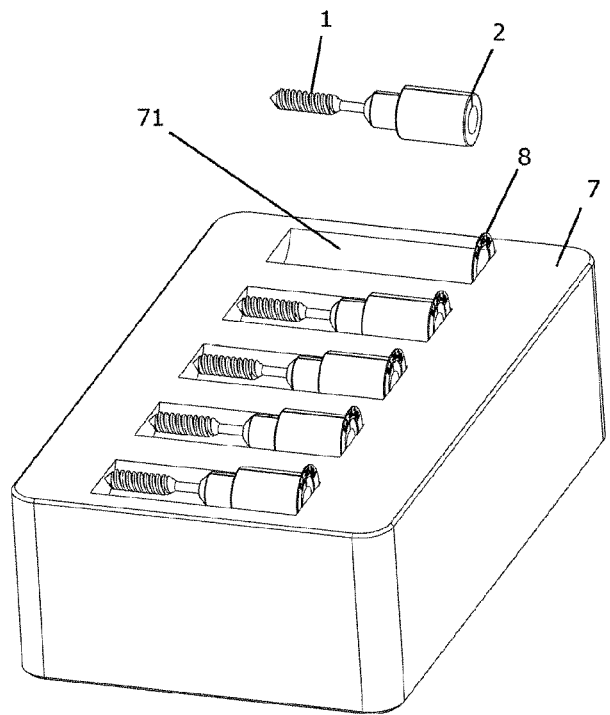
FIG. 9 is a perspective view showing another embodiment of a storage element including a plurality of cavities that each receive a gripper associated with an implant, with the tracer element sandwiched between the gripper and the storage element.
Figure 10:
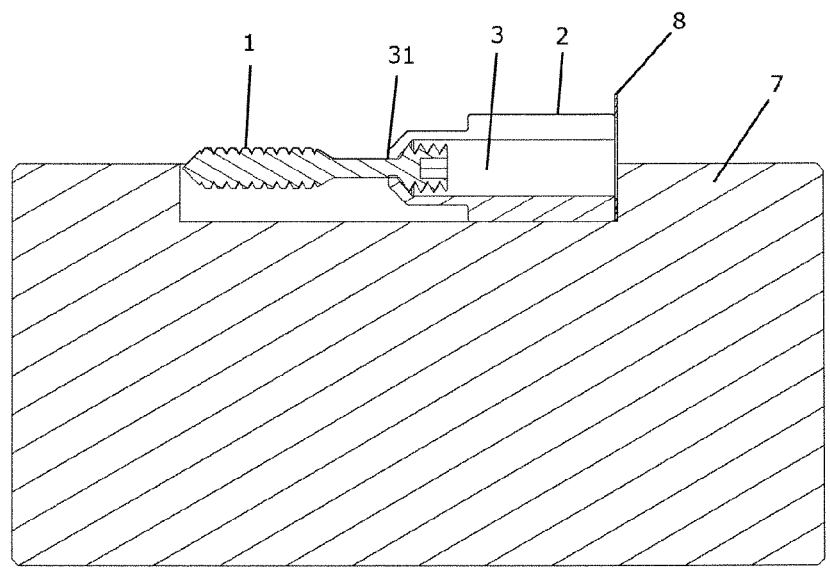
FIG. 10 is a section view of FIG. 9.

In the embodiment in FIGS. 9 and 10, the storage element 7 includes five cavities 71.

In the embodiment shown in FIGS. 1 to 6, each cavity is a cylindrical cavity of longitudinal axis that is substantially perpendicular to the surface of the plate.

The body 21 of the gripper 2 is inserted axially, via its distal end, into a cavity 3 until the outer peripheral shoulder 5 of said body forms an abutment that limits the extent to which the body can be inserted inside said location, by coming to bear against the top face of said plate.

In this embodiment, the zone of the gripper that extends between the distal end and the shoulder 5 of the gripper 2 is interfitted, at least in part, in the cavity 71 of the storage element 7, with the distal portion of the implant 1 that projects from the gripper 2 extending inside the cavity 71. As a result, the implant is completely masked from the outside.

In the embodiment shown in FIGS. 9 and 10, each cavity is a semi-cylindrical cavity of longitudinal axis that is substantially parallel to the surface of the plate. The gripper 2 and its implant 1 extend axially inside the cavity 71. In this way, they form a prone assembly inside said cavity.

The kit also includes a tracer element 8 that is sandwiched between the gripper 2 and the storage element 7 when the gripper 2 and its associated implant 1 are in their stored state in a reception cavity 71 of the storage element 7.

In this embodiment, the tracer element 8 is in the form of a washer that is provided with identification means for identifying the gripper 2. The washer has thickness that lies in the range 0.05 mm to 3 mm.

In the embodiment shown in FIGS. 1 to 6, the tracer element is sandwiched between the stepped surface of the gripper 2 and the top face of the plate.

The washer constituting the tracer element presents an inside diameter that is greater than the outside diameter of the gripper 2 in the zone of the gripper that extends between the distal end and the shoulder 5 of said gripper, and that is less than the outside diameter of the gripper 2 in the zone of the gripper that extends between the proximal end and the shoulder 5 of said gripper 2.

The washer thus surrounds the body of the gripper in the zone of the gripper that extends between the distal end and the shoulder 5 of the gripper, and is limited in axially movement along the body of the gripper by the shoulder 5 of said body 21.

As a result of this configuration, when the gripper and its associated implant are in their mounted state in a cavity of the storage element, the tracer element is masked at least in part. Thus, any risk of simultaneously taking hold of the tracer element while taking hold of the gripper is prevented.

In the embodiment shown in FIGS. 9 and 10, the tracer element 8 is sandwiched between the proximal end of the gripper 2 and the storage element 7, specifically between an end face of the semi-cylindrical cavity and the proximal end of the gripper.

Figure 2:
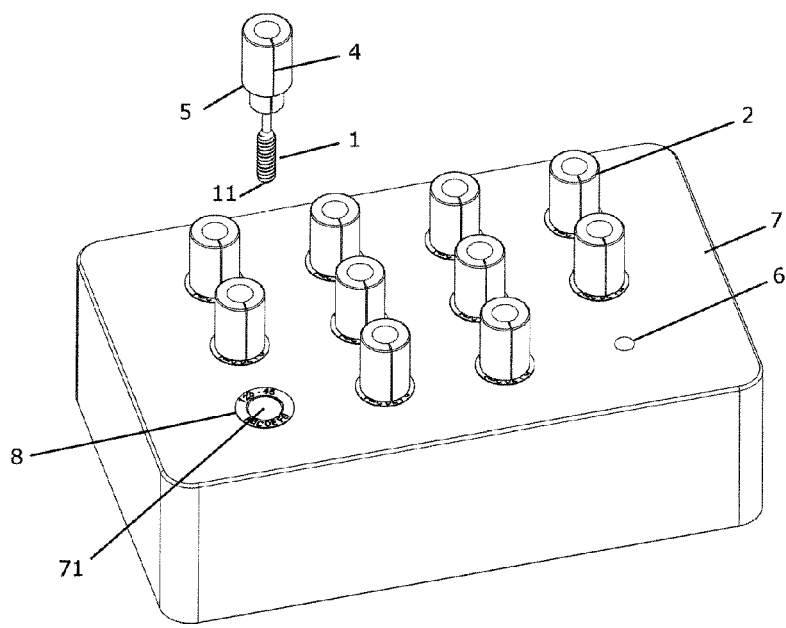
Figure 3:
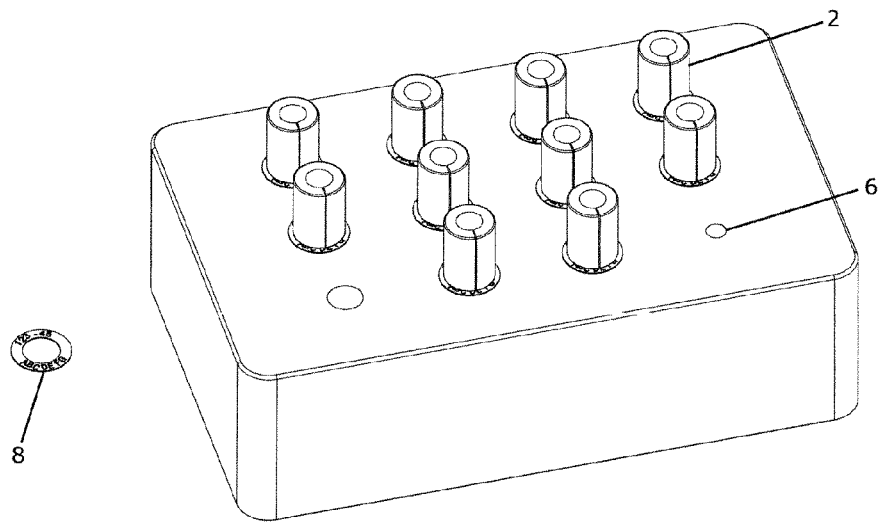
Figure 4:
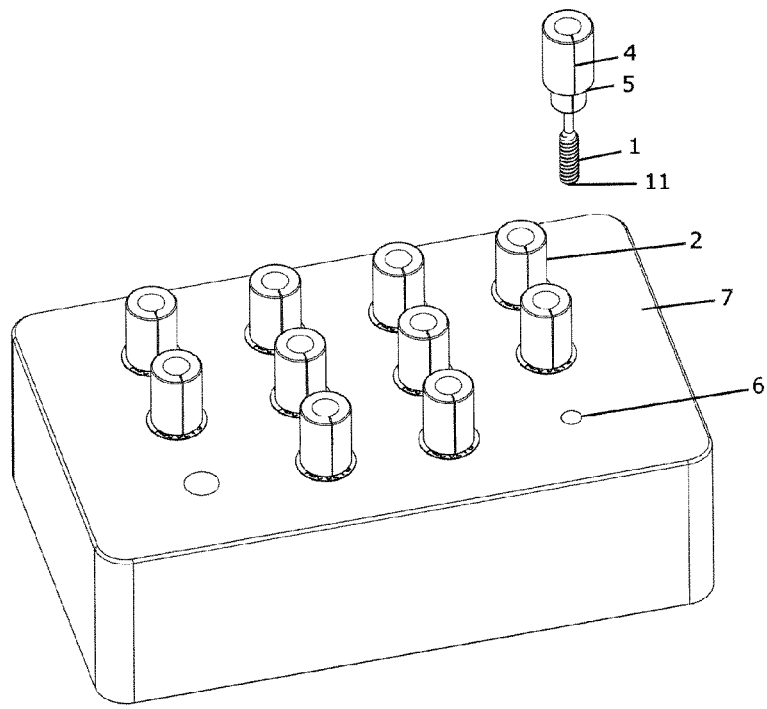
Figure 5:
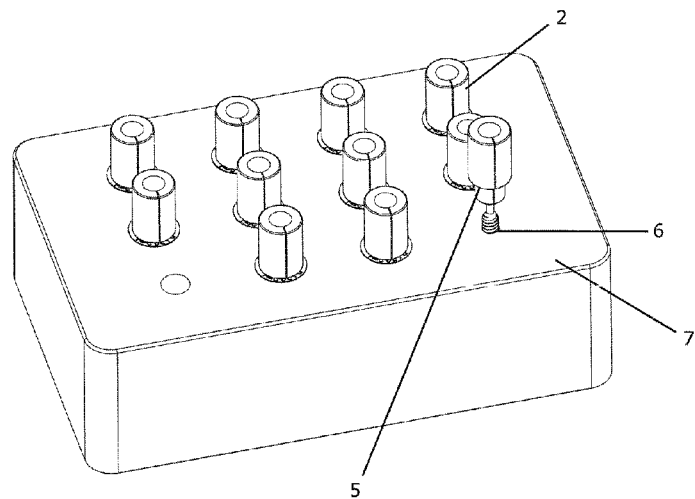

Independently of the storage-element embodiment, handling takes place as follows:

The implant and its gripper are housed, at least in part, in the storage element (FIG. 1), the gripper is taken hold of by an operator so as to remove the gripper and its associated implant from the storage element (FIG. 2). The tracer element 8 remains in its position around the cavity of the storage element from which the implant and its associated gripper have been removed. Such handling is made easier by the fact that the washer and the gripper are made of two incompatible materials so that they do not stick together. Thus, by way of example, the washer is made of metal, in particular of stainless steel, and the gripper is made of silicone rubber. These materials therefore do not stick together.

The tracer washer is of inside diameter that is much greater than the cavity of the storage element that receives the gripper, and that is much greater than the outside diameter of the gripper in the zone of the gripper that extends between the distal end and the shoulder of said gripper.

Since the inside diameter of the washer is also less than the diameter of the gripper between the shoulder and the proximal end of the gripper, the washer remains inaccessible so long as the gripper is not removed. It is thus practically impossible for the operator to remove the washer simultaneously with the gripper.

Under no circumstances can the gripper expand beyond the diameter of the cavity of the storage element, and thus it does not touch the washer while being extracted.

The small thickness of the washer prevents the washer from being gripped. In order to be removed or put into place, it is necessary to remove the gripper and its implant, and then press the washer against the surface of the plate and slide it so as to be able to put it into place or to remove it.

Consequently, at no time can the operator take hold both of the gripper associated with the implant and of the tracer element.

In the embodiment shown, once the gripper and its implant are removed from the storage element, the washer may be taken hold of manually with a view to reading information on said washer, and possibly transferring the information onto any medium.

In the embodiment in FIGS. 1 to 6, said kit also includes means for assisting in separating the gripper from the implant, preferably without touching the implant.

They comprise a sheath 6 for receiving the distal end 11 of the implant 1. The sheath is mounted securely to the storage element, and is formed by one of the cavities of the storage element. This cavity is of diameter that is less than the diameter of the other cavities. In particular, this cavity presents a diameter that is less than the outside diameter of the gripper.

Figure 6:
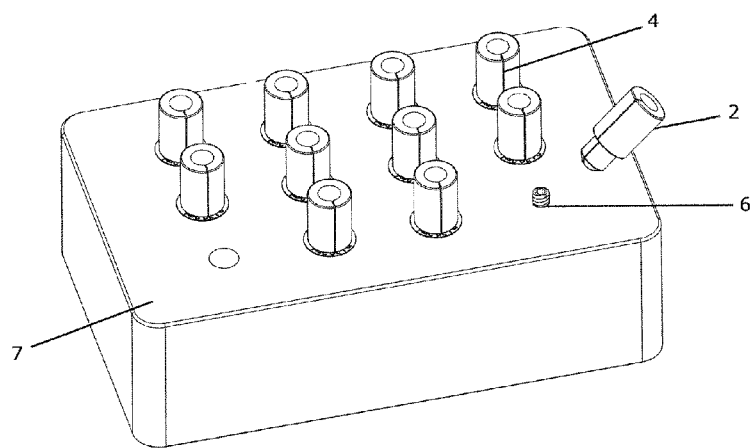
Figure 7:
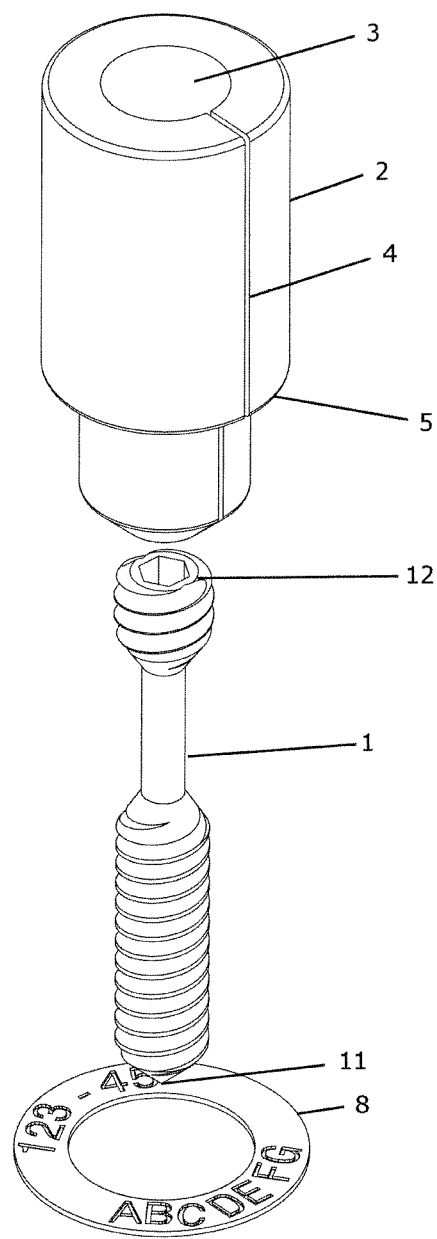
FIG. 7 is a perspective view showing the gripper, the implant, and the tracer element of a kit of the invention in the exploded position of said elements.

When the distal end 11 of the implant is in its inserted state in the sheath 6, the implant is separable from its gripper 2 by moving the sheath 6 and the gripper relative to each other in the direction that breaks the alignment between the sheath 6 and the gripper 2, as shown in FIG. 6, until the implant 1 passes through the slot 4 of the gripper 2.

The sheath 6 is provided with a bearing seat 61 against which the implant 1 bears both when said implant 1 is in its inserted state in the sheath 6, and when said implant 1 is in its state separated from its gripper. In this embodiment, the seat is formed by the free end of the sheath via which the implant is inserted inside the sheath.

Figure 8:
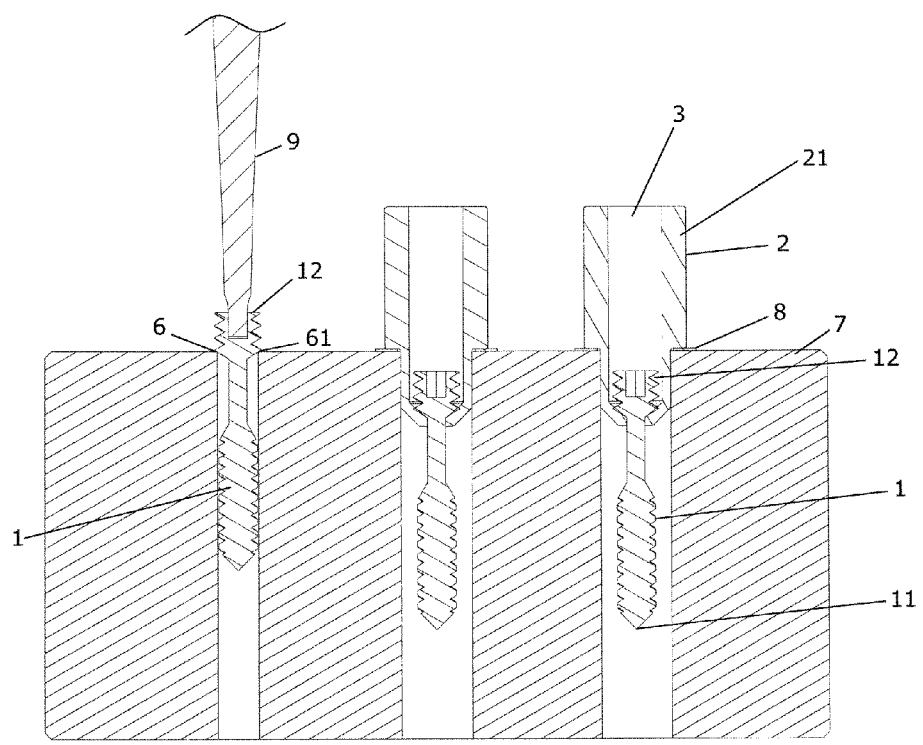
FIG. 8 is a section view showing a storage element including two cavities that each house an implant associated with a gripper, with the tracer element sandwiched between the gripper and the storage element, and a sheath housing an implant that is in its state separated from its gripper and that is coupled to a handling tool, such as a screwdriver.

The implant is thus held in abutment in the sheath and may be coupled to a handling tool 9, as shown in FIG. 8. Such coupling would not be possible if the implant remained inside the gripper as a result of the elastic deformation of the gripper, which elastic deformation makes any coupling of the implant and the handling tool difficult, with a high risk of imperfect or faulty coupling, possibly causing the implant to be lost or the implant to be turned poorly.

Once the implant and its handling tool are coupled to each other, implantation may be take place.

The procedure, as described above, may also be applied to the embodiment in FIGS. 9 and 10.

The procedure, as described above, shows that it is possible to transfer the implant from its storage element into the human or animal body without the surgeon's hand coming into contact with said implant at any time.

As a result, the risk of contamination is reduced.

The invention claimed is:

1. A kit comprising:
   an implant,
   a gripper configured to grip said implant, and
   a storage container stores the gripper and said implant,
     said storage container including at least one reception location that receives the gripper and said implant,
     said storage container having a tracer element configured to trace the implant; wherein the tracer element is sandwiched between the gripper and the storage container, when the gripper and said implant are in a stored state in a reception location in said storage container wherein the implant has a distal end for inserting the implant into a human or animal body, and a proximal end, that co-operates with a handling tool, wherein the gripper, that is separable from the implant, is a hollow elongate body that is open at one of its ends, and that has a slot positioned longitudinally along at least a portion of its length, the hollow elongate body made of, at least in part, an elastically-deformable material that biases edges of the slot towards each other, the slot of said hollow elongate body opening out into an axial cavity of said hollow elongate body, inside which the implant is inserted, with said distal end of said implant projecting from a distal end of said hollow elongate body, and the storage container includes a plate with at least one cavity that corresponds to said reception location of said gripper and said implant.

2. A kit according to claim 1, wherein the tracer element is a washer with an identification means that identifies the gripper.

3. A kit according to claim 2, wherein the washer presents is between 0.05 mm to 3 mm thick.

4. A kit according to claim 1, wherein the cavity that corresponds to the reception location for said gripper and said implant, has a longitudinal axis substantially orthogonal to a surface of said plate, wherein the hollow elongate body of the gripper, inserted axially said via distal end into the cavity, is a stepped tubular body with an outer peripheral shoulder, said outer peripheral shoulder, from the distal end towards a proximal end of said hollow elongate body forms an abutment that limits an extent to which the hollow elongate body can be inserted inside said reception location of the storage container, and wherein the tracer element is sandwiched between the stepped tubular body of the gripper and a top face of the plate.

5. A kit according to claim 1, wherein the tracer element is a washer with an identification means for identifying the gripper, the washer having an inside diameter that is greater than an outside diameter of the gripper in a zone of the gripper that extends between the distal end of the hollow elongate body and a shoulder of said gripper, and that is less than an outside diameter of the gripper in a zone of the gripper that extends between a proximal end of the hollow elongate body and the shoulder of said gripper.

6. A kit according to claim 1, wherein a zone of the gripper that extends between the distal end of the hollow elongate body and a shoulder of said gripper is interfitted, at least in part, in said cavity of the storage container, with the distal end of the implant that projects from the gripper extending inside said cavity.

7. A kit according to claim 1, wherein the cavity that corresponds to said reception location of said gripper and said implant, has a longitudinal axis substantially parallel to a surface of said plate, in that the gripper and said implant extend axially inside the cavity, and the tracer element is sandwiched between a proximal end of the gripper and the storage container.

8. A kit according to claim 1, wherein said kit further comprises a means for assisting in separating the gripper from the implant without touching the implant, the means comprising at least one reception sheath for receiving the distal end of the implant, and when said distal end of said implant is in an inserted state in the sheath, the implant is separable from said gripper by moving the sheath and the gripper relative to each other in a direction that breaks an alignment between the sheath and the gripper, until the implant passes through a slot in the gripper, said sheath having a bearing seat against which the implant bears both when said implant is in an inserted state in the sheath, and when said implant is in a state separated from said gripper.

\* \* \* \* \*